United States Patent [19]

Boitiaux et al.

[11] Patent Number: 5,336,829
[45] Date of Patent: Aug. 9, 1994

[54] CONTINUOUS PROCESS FOR THE DEHYDROGENATION OF PARAFFINIC TO OLEFINIC HYDROCARBONS

[75] Inventors: Jean-Paul Boitiaux, Poissy; Jean De Bonneville, Rueil Malmaison; Jean-Pierre Burzynski, Sainte-Foy-Les Lyon; Gérard Leger, Caluire; Fabienne Le Peltier, Rueil Malmaison; Germain Martino, Poissy, all of France

[73] Assignee: Institut Francais Du Petrole, Rueil Malmaison, France

[21] Appl. No.: 37,117

[22] Filed: Mar. 25, 1993

[30] Foreign Application Priority Data

Mar. 26, 1992 [FR] France .................. 92 03790

[51] Int. Cl.$^5$ .................................................. C07C 5/333
[52] U.S. Cl. ........................................ 585/659; 585/660; 585/661
[58] Field of Search ............................. 585/659, 660, 661

[56] References Cited

U.S. PATENT DOCUMENTS

| | | | |
|---|---|---|---|
| 3,531,543 | 9/1970 | clippinger et al. | 260/683.3 |
| 3,978,150 | 8/1976 | McWilliams, Jr. | 260/683.3 |
| 4,104,317 | 8/1978 | Antos | 585/660 |

FOREIGN PATENT DOCUMENTS 0212850  3/1987  European Pat. Off. .
2310399 12/1976  France .

Primary Examiner—Anthony McFarlane
Assistant Examiner—Nhat D. Phan
Attorney, Agent, or Firm—Millen, White, Zelano & Branigan

[57] ABSTRACT

A continuous process for the dehydrogenation of paraffinic and olefinic hydrocarbons in the presence of a catalyst comprises circulating a charge containing said paraffinic hydrocarbons through at least two reactions zones of the moving bed type which are arranged in series, the catalyst flowing successively in each reaction zone. The catalyst which is drawn off from the last reaction zone is sent to a regeneration zone at the exit from which it is reintroduced close to the first reaction zone. The process comprises the injection of sulphur and/or at least one sulphur compound before or simultaneously to the introduction of the charge into the first reaction zone. In accordance with the process, the catalyst which is drawn off from the last reaction zone is sent into a stripping zone wherein the sulphur which it contains is removed before the catalyst is sent to the regeneration zone.

10 Claims, 1 Drawing Sheet

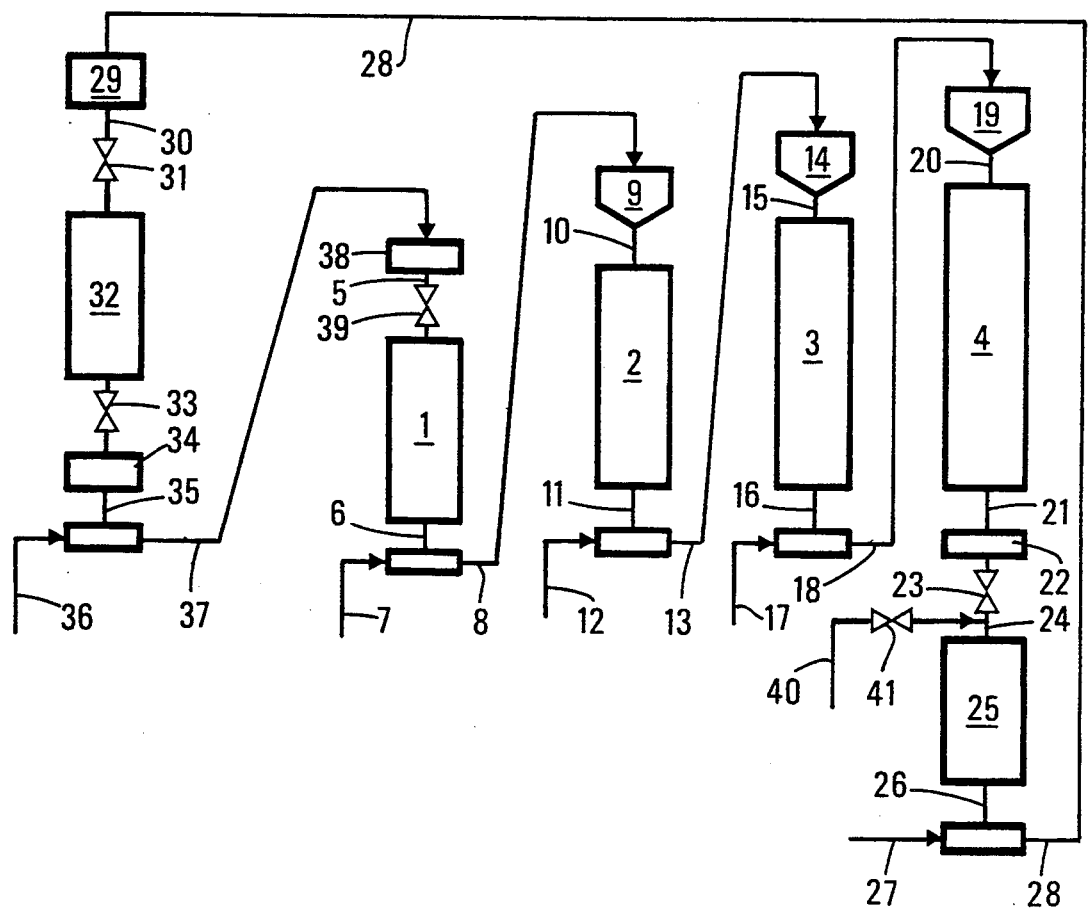

CONTINUOUS PROCESS FOR THE DEHYDROGENATION OF PARAFFINIC TO OLEFINIC HYDROCARBONS

BACKGROUND OF THE INVENTION

The invention relates to a continuous process for the dehydrogenation of paraffinic hydrocarbons, most frequently those hydrocarbons which are gaseous at ambient temperature, comprising at least 2 carbon atoms per molecule, into corresponding olefinic hydrocarbons.

The present invention concerns, more particularly, the synthesis of isobutene by the dehydrogenation of isobutane. Isobutene is used, in particular, fop the preparation of MTBE (methyl tertio-butyl ether) for the purpose of improving the octane index of gasolines.

The process of the present invention comprises means for injecting sulphur into the charge to be treated and means for stripping the sulphur which is retained on the catalyst; these conditions make it possible for the stability of the catalyst to be improved and also its life.

There is substantial interest in the implementation of dehydrogenation processes with hydrocarbons, such processes being effective, selective and economical while also contributing to the formation of hydrogen, a product which tends to be lacking in current refining operations. This interest is especially justified by the valorization of saturated hydrocarbon cuts, in particular, of low boiling saturated aliphatic hydrocarbons, such as ethane, propane, butane, isobutane, pentane and isopentane, which are recoverable, in particular, after the removal of unsaturated substances from C3, C4 and C5 cuts which have been obtained by steam-cracking or catalytic cracking, and also from liquefied petroleum gases, often called LPG, or from field gases.

The reaction for the production of olefinic aliphatic hydrocarbons, often called alkenes by chemists, from saturated aliphatic hydrocarbons, often called alkanes by chemists, has been known for a very long time. This reaction has been described, in particular in the patents U.S. Pat. Nos. 3,126,426, 3,531,543, 3,978,150, 4,381,417, 4,381,418, and U.S. Pat. No. 4,704,497. It can employ a metal catalyst supported on a platinum base, a chromium oxide on alumina or a crystalline zeolitic catalyst with a silica and alumina base of the MFI type.

One of the problems to be resolved concerns the coking content of the reactor materials, lines and inter-reactor exchangers; in fact, under the reaction conditions (increased temperature and presence of olefins) the customary materials catalyze the dehydrogenation reactions and cause relatively fast coking of the metal surface.

This fact is particularly critical in instances where the operation is carried out in a regenerative system, that is to say continuously, for in these instances it is not possible to interrupt the functioning of the reactors to mechanically decoke them or to burn the coke, without changing the nature of the process altogether.

SUMMARY OF THE INVENTION

It has been surprisingly discovered that by adding sulphur to the charge it is possible to render inert the metal surfaces without severely harming the process, and, in particular, without harming the conversion and selectivity into olefins.

Overall, the reaction is endothermic, and the reaction speed is sensitive to temperature variations, and the various reactions are accompanied by a deposit of coke on the catalyst, and, to a certain extent, by fritting Of the metal particles contained in the catalyst, which quite rapidly de-activates and reduces the life of the catalyst.

Another problem is the powerful de-activation of the catalyst at the high reaction temperatures. It has been noted that the addition of sulphur to the charge, or pre-sulphurisation of the catalyst is one possible way of improving its stability.

The catalyst can be regenerated in a cyclic system of continuously (by regeneration).

The invention relates to a continuous process fop the dehydrogenation of paraffinic hydrocarbons having at least two carbon atoms in their molecule into olefinic hydrocarbons in the presence of a catalyst, wherein a charge containing said paraffinic hydrocarbons is circulated through at least two reaction zones arranged in series, each of these reaction zones being of the moving bed type, the charge circulating successively through each reaction zone and the catalyst also circulating successively through each reaction zone flowing continuously of intermittently from a first end of said zone to its opposite end, the catalyst which is drawn off from the end of each reaction zone (except the last) being conveyed in a gas flow to the first end of the following reaction zone, the catalyst which is drawn off from the last reaction zone through which the charge passes then being sent to a regeneration zone at the outlet of which the regenerated catalyst is reintroduced continuously of intermittently close to the first end of the first reaction zone, said process comprising injection of sulphur and-/of at least one sulphur compound before of simultaneously to the introduction of the charge into the first reaction zone and being characterised in that the catalyst which is drawn off from the last reaction zone through which the charge passes is sent continuously or intermittently into a stripping zone wherein the sulphur which it contains is removed by stripping by means of a gas of a gas mixture, before the catalyst is sent continuously of intermittently into the regeneration zone.

The gas fop conveyance between the reactors can be hydrogen, nitrogen of a mixture of the two gases.

More particularly, the present invention relates to the production of olefinic hydrocarbons from a charge comprising saturated aliphatic hydrocarbons, most frequently having from 2 to 5 carbon atoms and preferably 3 to 5 carbon atoms in their molecule. These hydrocarbons can be propane, n-butane, n-pentane, butane isomers and pentane and mixtures thereof.

The process comprises means for injecting sulphur into the charge to be treated and means for stripping the sulphur retained on the catalyst, for this surprisingly makes it possible to improve the stability of the catalyst and also its longevity without having any significant effect upon the selectivity of the olefins.

In the process of the invention, the charge can be pre-mixed, or not, with a diluent selected, for example, from the group formed by hydrogen, water vapour and methane.

The charge circulates through at least two elementary catalytic zones arranged in series, most often vertical zones with intermediate heating between each zone; these catalytic zones are most frequently each constituted of a moving bed with radial flow. These zones are identical, for example, to those described in .the patent U.S. Pat. No. 4,277,444. The pressure in the catalytic zones is kept as low as possible, compatible with the losses of charge from the lines, the reactors and exchangers in such a way that advantage can be made of thermodynamic equilibrium. Sulphur can be injected into the charge in the form of sulphur and/or in the form of at least one compound of sulphur.

Most frequently, an organic sulphur compound is introduced into the charge. The organic sulphur compounds which are usually injected are selected from the group formed of organic disulphides and polysulphides, preferably those of the formulae $R^1$—$(S)_n$—$R^2$ wherein $R^1$ and $R^2$, which can be the same or different, each represent a hydrogen atom or a hydrocarbon radical and n is a number between 2 and 20 (inclusive) and preferably between 2 and 8 (inclusive).

Examples of hydrocarbon radicals are saturated or unsaturated, linear or branched aliphatic radicals, cycloaliphatic radicals and aryl radicals. In the above formula, $R^1$ and $R^2$ which are identical or different may represent independently of one another a hydrogen atom, a linear or branched alkyl radical, an aryl radical, an arylalkyl radical or a cycloalkyl radical.

It is advantageous to use polysulphides of the above formula, wherein at least one of the $R^1$ and $R^2$ radicals represents a hydrocarbon radical, and preferably those wherein $R^1$ and $R^2$ which are the same or different each represent a hydrocarbon radical such as a linear or branched alkyl radical or an aryl radical, for example. Organic polysulphides which are particularly preferred are those wherein $R^1$ and $R^2$ which may be the same or different, each represent an alkyl radical; they will be called dialkylpolysulphides hereinafter.

Examples of organic polysulphides can be cited as organic disulphides and more particularly dialkyldisulphides.

The organic polysulphides used in the present invention usually have from 2 to 72 carbon atoms, preferably 2 to 48 carbon atoms in their molecule.

The dialkylpolysulphides used advantageously have from 2 to 24 carbon atoms in their molecule and the organic polysulphides of the formula hereinabove wherein $R^1$ and $R^2$ represent an aryl, aralkyl or cycloalkyl radical advantageously have 6 to 48 carbon atoms, and preferably 10 to 32 carbon atoms in their molecule.

As examples of organic polysulphide specific compounds it is possible to cite dimethyldisulphide (DMDS), diethyldisulphide (DEDS), dipropyldisulphides, dibutyldisulphides, and, in particular, ditertiobutyldisulphide (DTBDS), diphenyldisulphide (DPDS), ditertiododecylpolysulphide (n=5) marketed by ELF AQUITAINE, for example, under the name TPS 32, in particular because it contains about 32% by weight of sulphur, and ditertiononylpolysulphide (n=5) marketed by ELF AQUITAINE, for example, under the name TPS 37.

The amount of polysulphide used in the present invention and expressed by weight of sulphur in relation to the charge is usually from 1 to 1000 ppm, and most frequently from 1 to 200 ppm. This amount is preferably about 5 to 100 ppm.

In each vertical zone, the catalyst moves slowly and is drawn off continuously or intermittently from the last catalytic zone to be sent into a regeneration zone at the exit from which the regenerated catalyst is sent back at the top of the first catalytic zone in order to maintain a substantially constant activity in each of the zones.

Appropriate frequencies and flow rates are used for drawing off the catalyst coming from the last catalytic zone. The catalyst can be drawn off, for example, either continuously or intermittently at a frequency of 1/10 to 10 days, only drawing off a fraction at a time, such as for example, 0.5 to 15% of the total amount of catalyst. It is also possible to draw off this catalyst at a much faster frequency in the order of a minute or a second; the amount drawn off is then reduced proportionately.

The spent catalyst, or partly spent catalyst, which comes from the last catalytic zone is then directed to a stripping zone where sulphur which has accumulated in the reaction zones is removed. This operation is carried out by injecting a stripping fluid at a temperature of between 400° C. and 700° C. preferably between 500° C. and 600° C. at a pressure of between 1 and 4 bar, preferably of between 1.5 and 2.5 bar, and at a VVH of between 100 $h^{-1}$ and 4,000 $h^{-1}$, preferably between 700 and 2,500 $h^{-1}$.

The stripping fluid is usually selected from the group formed by substantially pure hydrogen, the hydrogen containing 5 to 10,000 ppm by weight of water and/or from 5 to 5,000 ppm by weight of a halogen, substantially pure nitrogen, the nitrogen containing from 5 to 10,000 ppm by weight of water and/or from 5 to 5,000 ppm by weight of a halogen, the mixtures of substantially pure nitrogen and substantially pure hydrogen and the mixtures of nitrogen and hydrogen containing from 5 to 10,000 ppm by weight of water and/or from 5 to 5,000 ppm by weight of a halogen. This halogen is most frequently chlorine.

In a first variant, the stripping fluid can preferably be recycling hydrogen which is possibly purified of sulphur from the charge or from the catalyst if this latter has been pre-sulphurised. The catalyst in the stripping zone can be disposed in an axial or radial bed.

The stripping operation can be carried out continuously or intermittently.

The catalyst from which sulphur is removed can then be ascended in a lift to an "accumulator decanter" round bottomed flask disposed above the regenerator. The fluid of the lift which is used to convey the catalyst can preferably be recycling hydrogen. In the round bottomed "accumulator decanter" flask, the hydrogen is separated from the catalyst and is directed towards a filter to remove fine particles of catalyst, and is thence sent to a compressor for recycling, to a reaction space, for example, to the lifts or stripping zone.

According to one variant of the process, the stripping zone can be placed after the "accumulator decanter" round bottomed flask and in front of the actual regenerator.

The catalyst can be regenerated discontinuously or continuously using any known means. The regeneration zone must be kept free of any trace of hydrogen during the regeneration phase. In discontinuous mode, the spent catalyst, or partially spent catalyst, accumulates in the "accumulator decanter" found bottomed flask before supplying the regenerator which is usually disposed below the round-bottomed flask. At regular intervals, the regenerator is placed in equilibrium of pressure in an atmosphere of hydrogen, for example, with the "accumulator decanter" round-bottomed flask; it is then filled with catalyst which comes through a system of valves in the "accumulator decanter" round-bottomed flask and is then isolated from the rest of the system. The regenerator is then purged with nitrogen to remove the hydrogen and the hydrocarbons, and the catalyst is regenerated. The regenerator, or an accumulator round-bottomed flask in which the regenerated catalyst has been transferred is then purged with nitrogen and is then placed with hydrogen in an equilibrium of pressure with the catalytic zone, in which the catalyst is going to be injected.

The actual regeneration operation, particularly in the case of a catalyst on an alumina support, is usually carried out in the following way:

- a first treatment corresponds to the combustion of coke deposits. This operation is carried out by injecting air into an inert mixture (composed, for example, of nitrogen and carbonic gas), this inert mixture acting as a thermal diluent. The oxygen content in the regeneration gas injected at the top of the regenerator is preferably between 0.01 and 2% by volume. The injected air is consumed by combustion of the coke deposits, and the end of the combustion process is easily detected by the increase in oxygen content in the gas issuing from the regenerator and also by the disappearance of the front of the flame (horizontal plane where the combustion is produced) which is propelled from the top to the bottom of the catalytic bed. Combustion is carried out at an average temperature which is preferably between 350° and 550° C. and at a pressure of between 1 and 15 bar, for example.
- a second treatment corresponds to oxychlorination of the catalyst; to this end, the amount of oxygen of the regeneration gas admitted into the regenerator preferably being less than 10% in relation to the value in the first stage. The oxygen content is most frequently between 1 and 8% volume during this oxychlorination step. During this step, a halogen and/or a halogenated compound is introduced simultaneously. Chlorine and/or a compound with chlorine is/are preferably used. An alkyl halogenide is preferably used which contains 1 to 6 carbon atoms per molecule, preferably carbon trichloroethane or carbon tetrachloride. The proportion of halogen or halogenated compound used is such that it can be capable of forming 0.2 to 1.2% by weight of a halogenated derivative of alumina in relation to the catalyst undergoing regeneration; oxychlorination is carried out at a temperature of between 350° and 550° C. and at a pressure of between 1 and 15 bar. This treatment can last between 20 minutes and three hours. It usually lasts about one hour;
- a third treatment corresponds to oxidation of the catalyst: to carry it out, the amount of oxygen of the regeneration gas admitted into the regenerator is increased again, preferably by at least 10% in relation to the previous step. The oxygen content is thus most frequently between 3 and 20% by volume, the average temperature being between 350° and 550° C. and the pressure being between 1 and 15 bar. This operation lasts between 30 minutes and two hours, for example. It usually lasts one hour.

These three treatments are usually carried out either successively in one single chamber with a fixed bed, for example, or in a chamber with a moving bed, the catalyst passing through three separate zones in succession where each of the regeneration steps are carried out. These treatments can also be carried out successively in a plurality of separate chambers.

The catalyst is then transferred from the regenerator to the first catalytic zone, through a system of valves. At the top of this catalytic zone, the catalyst is first of all collected in a space separate from the reaction zone (that is to say where no reaction mixture containing hydrocarbons passes) where it is reduced by a hydrogen flow at a temperature of between 350° and 600° C. and at a pressure of between 2 and 25 bar, preferably between 4 and 15 bar. The catalyst may be presulphurised in this space. The fresh (and reduced) catalyst gradually supplies the selected reaction zone as the spent catalyst is drawn off.

In a second variant, the stripping fluid comprises nitrogen. According to this variant of the process, the spent catalyst, or partly spent catalyst, which comes from the last catalytic zone is conveyed with nitrogen to the stripping zone so that sulphur collected in the reaction zones can be removed. In this case, the stripping takes place in an atmosphere of nitrogen at a temperature of between 400° and 700° C., preferably between 500° and 600° C., at a pressure of between 1 and 4 bar, preferably 1.5 and 2.5 bar and at a VVH of between 100 $h^{-1}$ and 4,000 $h^{-1}$, preferably 700 and 2,500 $h^{-1}$ The catalyst in the stripping zone can be disposed in axial or radial fixed bed. The stripping can be carried out continuously or intermittently.

In this variant, the catalyst from which sulphur is removed is ascended by a lift with nitrogen to an "accumulator decanter" round-bottomed flask which is arranged above the regenerator, for example. In the "accumulator decanter" round-bottomed flask, the nitrogen is separated from the catalyst and conveyed to a filter to remove the fine particles of catalyst, and is thence sent to a compressor to be recycled towards the lifts or stripping zone, for example. The regeneration is carried out in the same way as described hereinabove in connection with the first embodiment, except that the regenerator is placed in an equilibrium of pressure with the "accumulator decanter" found-bottomed flask which is carried out in an atmosphere of nitrogen. This second variant allows the purging phase with nitrogen of the regenerator and/or of the accumulator round-bottomed flask whence regenerated catalyst has been transferred to be abandoned. In this variant, at the end of the regeneration step, the catalyst is transferred, still in an atmosphere of nitrogen, to a space which is separate from the reaction zone (that is to say wherein the reaction mixture containing the hydrocarbons does not pass) where it is reduced, by a current of hydrogen, at a temperature of between 350° and 600° C. and at a pressure of between 2 and 25 bar, preferably between 4 and 15 bar. Presulphuration of the catalyst can possibly be carried out in this space. The fresh (and reduced) catalyst is then supplied gradually to the selected reaction zone as the spent catalyst is withdrawn.

The dehydrogenation reaction is usually carried out at a pressure of between 0.2 and 20 bars absolute (1 bar=0.1 MPa) and at a temperature of 400° to 800° C. depending on the type of charge, the temperature advantageously being between 540° and 700° C. for propane and between 500° and 650° C. for the cut containing isobutane at a pressure which is preferably between 1 and 4 bars absolute. The volumetric spatial speeds (relative to the liquid charge) recommended are usually between 0.5 and 20 $h^{-1}$ and preferably between 1.5 and 6 $h^{-1}$. When the charge comprises hydrogen, its recycling rate is between 0 and 10 moles of hydrogen per mole of charge.

The catalyst used in the present invention can be any conventional dehydrogenation catalyst well-known to those skilled in the art. This catalyst is preferably a catalyst composed of grains, having, on a support selected from the group formed by alumina and zeolites, at least one group VIII noble metal, at least one group IVA metal, and at least one group IA or IIA metal, preferably a group IA metal. The grains of catalyst are most frequently in the form of substantially spherical balls and their diameter is usually between 1 and 3 millimeters (mm) and preferably between 1.5 and 2 mm. The specific surface area of the support is most frequently between 20 and 800 square meters per gramme ($m^2/g$) and preferably between 50 and 500 $m^2/g$. The catalyst most frequently contains, by weight in relation to the support, 0.01 to 2% of at least one noble group VIII metal, 0.01 to 3% of at least one group IVA metal and from 0.1 to 3% of at least one group IA or IIA metal. A particularly preferable catalytic formula includes, on a support of alumina, platinum, tin and potassium. The catalyst can also contain a halogen or a halogenated compound such as chlorine, for example, or a chlorine compound. It can also contain sulphur.

BRIEF DESCRIPTION OF FIGURE

The attached figure is a schematic flowsheet of a comprehensive embodiment of the invention, but without limiting the scope thereof. In the figure, the reaction zones are substantially vertical and the catalyst circulates from the top to the bottom in each of these zones, and is conveyed by a hydrogen current from the bottom of a given zone (with the exception of the last zone) to the top of the following zone.

In the figure, for the sake of simplicity, the path of the charge circulating successively through the reactors in series (1, 2, 3 and 4) has not been illustrated.

DETAILED DESCRIPTION OF FIGURE

The charge enters at the top of the reactor (1) and leaves it at the bottom to be reintroduced at the top of the reactor (2), and so on and so forth in the reactors (3) and (4). Between each reactor, the charge passes through a heating means, not shown in the drawing. The catalyst which is introduced through the conduit (5) at the top of the reactor (1) is drawn off through the conduit (6) and then transferred to the recipient (9) disposed above the reactor (2) by means of a lift (8), the motor fluid of which is recycling hydrogen, coming from the reaction section, introduced by the conduit (7). The catalyst contained in the recipient (9) is introduced into the top of the reactor (2) through the conduit (10). The catalyst passes likewise through the reactors (2), (3) and (4).

The spent catalyst which is drawn off through the conduit (21) at the bottom of the reactor (4) is directed towards the regeneration zone (32). In a first variant, passage from an atmosphere of hydrogen to an atmosphere of nitrogen is directly upstream of the regenerator at the level of the "accumulator decanter" round-bottomed flask (29), and return to an atmosphere of hydrogen is directly downstream of the regenerator at the level of the accumulator round-bottomed flask (34), and sealing is provided by valves (31) and (33) (in reality, there are most frequently many valves (31) and (33)), whilst in a second variant the hydrogen/nitrogen transition takes place at the outlet from the reactor (4) at the level of the accumulator round-bottomed flask (22), nitrogen/hydrogen transition takes place directly upstream of the first reactor (1) at the level of the round-bottomed flask (38), and sealing is provided by valves (23) and (39) (most frequently, the valves are a system of multiple valves (23) and (39)). The spent catalyst is sent via the conduit (24) into the stripping zone (25) where it undergoes stripping with heat by means of one of the stripping gases described hereinabove (hot hydrogen or hot nitrogen, for example) to remove therefrom part of the sulphur which has accumulated in the reaction zones. The catalyst from which sulphur has been removed and which has been drawn off through the conduit (26) is then ascended by a lift (28), the motor fluid of which is recycling hydrogen in a first variant and nitrogen or a gas containing nitrogen in a second variant which is introduced partly through the conduit (40) and the valve (41) and partly through the conduit (27) to the "accumulator decanter" round-bottomed flask (29).

In this round-bottomed flask (29), the motor fluid, after having been separated from the catalyst, is sent through a conduit, not shown, to a recycling compressor through a system for filtering the fine catalyst particles. The spent catalyst is then conveyed via the conduit (30) to the regenerator (32) which is placed in equilibrium of pressure in an atmosphere of the motor gas used (most frequently hydrogen or nitrogen) with the "accumulator decanter" round-bottomed flask (29). The regenerator is then isolated from the rest of the system by closing the valves (31) and (33), purged with nitrogen, if necessary (that is to say when the motor gas is not nitrogen), and the regeneration, consisting of the three treatments described hereinabove, is carried out there in one single chamber with fixed bed or in a chamber with a moving bed. When the regeneration is carried out, the regenerator (32) is purged with nitrogen, if necessary, and is then either placed in an atmosphere of hydrogen in equilibrium of pressure with the reactor (1), or is kept in an atmosphere of nitrogen; the regenerated catalyst is conveyed to a round-bottomed buffer flask (34), ascended through the conduit (35) and a lift (37) which operates by way of a motor gas introduced through the line (36) which is either hydrogen or nitrogen, depending on the case, into a collecting recipient for the catalyst (38) in which reduction and sulphuration of the catalyst can take place. The regenerated catalyst which is reduced and sulphurated is then gradually introduced into the reactor (1). The catalyst passes from the reactor (2) to the reactor (3), via the line (11), the lift (13) which is supplied with hydrogen via the line (12), the recipient (14) and the line (15). Likewise, it passes from the reactor (3) to the reactor (4), via the line (16), the lift (18) which is supplied with hydrogen via the line (17), the recipient (19) and the line (20).

The following examples which are non-limitative illustrate the advantage of the present invention, without, however, limiting the scope thereof. The examples are described in connection with the embodiment shown in the drawing.

4 reactors in series are used (see drawing). The catalyst issuing from the fourth reactor is regenerated.

The catalyst used in the examples is a conventional catalyst supported on alumina containing 0.6% by weight platinum, 0.9% by weight tin and 0.9% by weight potassium and 0.6% by weight chlorine.

The hydrocarbon charge which is treated has the composition given in Table I.

TABLE I

| Charge | % By Weight |
|---|---|
| Propylene | 0.09 |
| Propane | 1.24 |
| Isobutane | 92.57 |
| Isobutene | 0.02 |

TABLE I-continued

| Charge | % By Weight |
|---|---|
| n-butane | 6.00 |
| n-butenes | 0.05 |
| $C_{5+}$ | 0.03 |

Added beforehand to the charge (that is to say prior to its introduction into the first reactor) is a sufficient amount of DMDS to produce a charge containing 50 ppm by weight of sulphur. In each of the reactors, the temperature at the intake is 590° C. and the spatial volumetric speed is 2 volumes of the liquid charge (at 15° C.) per volume of catalyst and per hour. The recycling rate of the hydrogen is 1 mole of hydrogen per mole of charge. The pressure at the intake to the first reactor is 3.2 bar. These reactors are of the "radial" kind, such as those described in the patent U.S. Pat. No. 4,277,444.

The catalyst is distributed in reactors in the following weight ratios:
1) reactor: 22%,
2) reactor: 24%,
3) reactor: 26% and
4) reactor: 28%.

The total amount of catalyst is 22,350 kg. The catalyst is renewed at a rate of 150 kg/h. The flow rate of $H_2$ in the lifts 8, 13, 18, 28 and 37 is 15 kg/h.

EXAMPLE 1 (COMPARATIVE)

In this example, the spent catalyst coming from the last reactor does not pass through the stripping recipient (25) and is conveyed directly to the "accumulator decanter" round-bottomed flask (29) by the lift (28) in an atmosphere of hydrogen. The regeneration is carried out in the following way:

1) a first treatment corresponding to combustion of the coke, for which the temperature at the entry to the regeneration zone (32) is kept at 420° C., the pressure in the regenerator (32) is kept at 3.2 bar, the oxygen content of the gaseous mixture (nitrogen plus air) introduced is kept at 0.5% by volume, and the stay time in the zone is 1 h 30;

2) a second oxychlorination treatment for which the temperature at the entry to the zone is brought to 510° C., the pressure is kept at 3.2 bar, trichloroethane ($C_2H_3Cl_3$) being injected at a flow rate of 0.8 kg/h, the oxygen content of the oxychlorination gas at the entry to the zone being 5% by volume and the stay time of the catalyst being 1 h;

3) a third treatment corresponds to calcination, for which the temperature in the zone is 510° C., the pressure is kept at 3.2 bar, the oxygen content is 6% by volume and the stay time of the catalyst is 1 h.

The regenerator (32) is then purged with nitrogen and then placed in an atmosphere of hydrogen in equilibrium of pressure with the first reactor.

The catalyst is reduced in chambers (34) and (38) and the lift (37), the flow fate of the hydrogen being 90 kg/h, the temperature being kept at 530° C. and the pressure being kept at 5 bar; the stay time of the catalyst in the chamber is 2 hours.

The catalyst is deactivated rapidly during the cycles- This manifests itself by irreversible poisoning of the catalyst which causes a spectacular drop in conversion, a decrease in isobutene selectivity and consequently a noticeable decrease in the isobutene yield. The results obtained are shown in Table 2 below:

TABLE 2

| Operating Time (h) | Conversion $iC_4^* =$ (% weight) | Selectivity $iC_4^* =$ (% weight) | Yield $iC_4^* =$ (% weight) |
|---|---|---|---|
| 250 | 33.5 | 95.2 | 31.9 |
| 1250 | 31.7 | 93.7 | 29.7 |
| 1350 | 21.3 | 92.8 | 19.8 |
| 2300 | 16.3 | 90.7 | 14.8 |
| 2400 | 4.1 | 89.2 | 3.7 |

*$iC_4 =$ represents isobutene

EXAMPLE 2 (ACCORDING TO THE INVENTION)

A second batch of catalyst of the same formulation is prepared. The same device and the same conditions as those described in connection with Example 1 are used. The regeneration conditions are identical except that a stripping phase is carried out, in the recipient (25), of the spent catalyst coming from the last reactor, prior to the combustion, oxychlorination and calcination treatments. The stripping is carried out, with hydrogen, at a temperature of 580° C. at a volumetric spatial speed (relative to the gas) of 900 $h^{-1}$.

Under these conditions, the catalyst shows itself to be very stable during the cycles. This is manifested by the fact that conversion is at a high level, selectivity of isobutene of substantially constant during the cycles and consequently the isobutene yield is substantially constant over time. The results obtained are specified in Table 3 below:

TABLE 3

| Operating Time (h) | Conversion $iC_4^* =$ (% weight) | Selectivity $iC_4^* =$ (% weight) | Yield $iC_4^* =$ (% weight) |
|---|---|---|---|
| 250 | 38.0 | 95.2 | 36.2 |
| 1250 | 37.4 | 94.8 | 35.5 |
| 1350 | 37.1 | 94.1 | 34.9 |
| 2300 | 36.8 | 95.7 | 35.2 |
| 2400 | 37.2 | 94.9 | 35.3 |

$iC_4^* =$ represents isobutene

We claim:

1. A continuous process for the dehydrogenation of paraffinic hydrocarbons having at least two carbon atoms per molecule in the presence of a catalyst to form olefinic hydrocarbons, said process comprising:
introducing a charge containing said paraffinic hydrocarbons successively through a first and at least one other moving bed reaction zone arranged in series;
continuously or intermittently circulating the catalyst successively through each of the reaction zones from one end of a reaction zone to its opposite end;
withdrawing the catalyst from the opposite end of each reaction zone, except for the last reaction zone, and conveying the withdrawn catalyst with a gas to one end of the next reaction zone;
withdrawing the catalyst from the last reaction zone through which the charge passes and passing the withdrawn catalyst to a regeneration zone having an outlet; and
withdrawing regenerated catalyst from said outlet and reintroducing the regenerated catalyst continuously or intermittently to the first reaction zone, said process further comprising:

injecting at least one element selected from the group consisting of sulphur and compounds of sulphur into the first reaction zone before or simultaneously with the introduction of the charge;

continuously or intermittently passing said catalyst withdrawn from said last reaction zone into a stripping zone; and stripping the sulphur therefrom with a gas or gas mixture before said catalyst withdrawn from the stripping zone is passed continuously or intermittently into the regeneration zone.

2. A process according to claim 1, wherein the stripping gas comprises at least one element selected from the group consisting of substantially pure hydrogen, hydrogen containing 5 to 10,000 ppm by weight of water, hydrogen containing 5 to 5,000 ppm by weight of a halogen, substantially pure nitrogen, nitrogen containing 5 to 10,000 ppm by weight of water, and nitrogen containing 5 to 5,000 ppm by weight of a halogen.

3. A process according to claim 1, wherein an organic sulphur compound is injected into the charge.

4. A process according to claim 3, wherein the sulphur compound is selected from the group consisting of organic disulphides and polysulphides of formula $R^1$—$(S)_n$—$R^2$ wherein $R^1$ and $R^2$, which are the same or different, represent a hydrogen atom or a hydrocarbon radical and n is a number between 2 and 20.

5. A process according to claim 3, wherein the sulphur compound is selected from the group consisting of dimethyldisulphide, diethyldisulphide, dipropyldisulphides, dibutyldisulphides, diphenyldisulphide, ditertiododecylpentasulphide and ditertiononylpentasulphide.

6. A process according to claim 1, wherein the catalyst is a catalyst composed of particles comprising, on a support selected from the group consisting of alumina and zeolites, at least one group VIII noble metal, at least one group IVA metal, and at least one group IA or group IIA metal.

7. A process according to claim 6, wherein the catalyst contains by weight in relation to the support 0.01 to 2% of at least one group VIII noble metal, from 0.01 to 3% of at least one group IVA metal and from 0.1 to 3% of at least one group IA or group IIA metal.

8. A process according to claim 6, wherein the catalyst comprises platinum, tin and potassium on an alumina support.

9. A process according to claim 1, wherein the reaction zones are substantially vertical and the catalyst which circulates from the top to the bottom in each of these zones is conveyed by a hydrogen current from the bottom of a given zone with the exception of the last zone to the top of the following zone.

10. A process according to claim 1, wherein said charge comprises hydrogen.

* * * * *